United States Patent [19]

Saito et al.

[11] 4,217,107

[45] Aug. 12, 1980

[54] METHOD OF MEASURING BLOOD CLOTTING TIME

[75] Inventors: Yukio Saito; Koichi Sekiya; Masaaki Takahashi, all of Tokyo, Japan

[73] Assignee: Sankyo Company Ltd., Tokyo, Japan

[21] Appl. No.: 944,783

[22] Filed: Sep. 22, 1978

[30] Foreign Application Priority Data

Sep. 30, 1977 [JP] Japan .................. 52-118730

[51] Int. Cl.² ............... G01N 33/16; G06F 15/42
[52] U.S. Cl. ............... 23/230 B; 23/918;
23/926; 73/61.4; 356/39; 422/73
[58] Field of Search ............ 23/230 B, 918, 926;
422/73; 364/414, 415, 425, 426, 733; 356/39;
250/565; 73/61.4

[56] References Cited

U.S. PATENT DOCUMENTS

| 3,458,287 | 7/1969 | Gross et al. | 422/73 X |
| 3,658,480 | 4/1972 | Kane et al. | 422/73 X |
| 3,723,062 | 3/1973 | Dahms | 23/230 B |
| 3,754,866 | 8/1973 | Ritchie et al. | 422/73 |
| 3,814,585 | 6/1974 | Bailly | 422/73 X |
| 3,833,864 | 9/1974 | Kiess et al. | 422/73 X |
| 4,047,890 | 9/1977 | Eichelberger et al. | 422/73 X |

Primary Examiner—Michael S. Marcus
Attorney, Agent, or Firm—Frishauf, Holtz, Goodman & Woodward

[57] ABSTRACT

A blood clotting end point detector which includes means for monitoring an electrical signal representing the value A of one or more optical properties of a blood plasma sample to which a coagulating agent has been added, means for deriving the first and the second differentials with respect to time of the value A, means for detecting the moment Ta when the second differential changes from negative to positive or becomes positive, means for detecting the moment Tb when the second differential next changes from positive to negative, means for deriving the difference (R) between the tangent to the curve A at the moment Ta and the curve A, means for determining whether the difference (R) or the integral, with respect to time from moment Ta to moment Tb, of the difference (R) exceeds a predetermined threshold value, in which case moment Tb is taken as the true clotting end point.

7 Claims, 8 Drawing Figures

METHOD OF MEASURING BLOOD CLOTTING TIME

BACKGROUND OF THE INVENTION

In the present invention, an improvement is made to the clotting end point detector of a known blood clotting time measuring device to facilitate the accurate and consistent detection of the clotting end point to provide a reliable measurement of the blood clotting time.

Measuring blood coagulation or clotting time is necessary for caring for medical patients with tendencies to bleed and for controlling anti-coagulant therapy for thrombotic diseases. Representative techniques employed are Prothrombin Time measurement (PT) for checking the extrinsic coagulation system, Activated Partial Thromboplastine Time measurement (APTT) for the intrinsic system and Partial Thromboplastine Time measurement (PTT).

In the above mentioned PT technique a reagent (such as Simplastin manufactured by Warner-Lambert) is added to a plasma sample separated from the blood. An optical property of the sample is then monitored, such as (1) absorbance, (2) transmittance or optical decay ratio, (3) intensity or logarithm of the light scattered by the sample, (4) refractive index, or (5) the sum or difference of the above going (1), (2), (3) and (4). Hereinafter, the instantaneous value of the monitored optical property or properties will be designated as A. The moment when the detected value of A changes radically is taken as the point where clotting ends, and the time interval from when the reagent is added to when clotting ends is taken as the prothrombin time or PT.

In the APTT technique a reagent (such as Platelin-plus-activator manufactured by Warner-Lambert) is added to a plasma sample, which is reacted at 37° C. for a length of time specified for the reagent (such as for 5 minutes). Then a coagulant agent (such as a solution of calcium chloride) is added. As in the case of the PT technique, one or more optical properties of the sample are monitored, and the point where the value A changes radically is taken as "the clotting end point" and the time interval from when the agent is added to when clotting ends is taken as APTT. PTT is substantially the same as APTT.

The curve for the monitored value of A in respect of one or more optical properties of the plasma sample when a coagulating reagent has been added, changes gradually in the initial stage, changes more rapidly as clotting proceeds, and then finally converges to a certain value.

The difference between the value of A prior to coagulation and after the completion of coagulation varies and depends on the sample. In the case of absorbance, it is approximately 0.01–0.1 (Abs). Blood clotting time is taken by measuring the time from when the coagulating agent is added to when the optical properties of the sample change. Conventionally, two methods are used in detecting the point where the optical properties change or when clotting is completed.

The first method is to differentiate the curve A with respect to time and to detect when this differential dA/dt exceeds a certain predetermined threshold value, this moment being taken as the clotting end point. In this method, when the setting of the threshold value is changed relative to the chronological change in the value of A during clotting, then the moment detected as the clotting end point will also change. Accordingly, if the amplitude of the first differential of curve A changes, the clotting end point also changes. For this reason, threshold values have been set empirically in the prior art. In order to avoid the empirical factors considered undesirable for measuring the clotting time, the following method has been used.

The second method takes as the clotting end point not a predetermined gradient of curve A but the steepest part of this curve A. In other words, curve A is differentiated twice to obtain the second differential $d^2A/dt^2$ curve with respect to time. The point where the amplitude of this curve crosses zero from the positive side to the negative side is taken as the clotting end point. In this case, the clotting end point is determined by the optical properties of the sample alone because no threshold value is used and therefore no influence is exerted by the level at which threshold values are chosen. This second method, therefore, is advantageous in that no empirical factors enter in determining the clotting end point.

As has been explained above, the first and the second methods are useful for plasmas showing normal clotting time characteristics. Generally, blood coagulation tests should measure not only the clotting time but should also adjust the said clotting time with the activation curve or the relation of clotting time and coagulation factor concentration. In this case, the activating curve presents the relation between coagulation factor concentrations, or the concentrations of normal pooled plasma in the solution of normal plasma diluted with PSS (physiological saline solution), fiblinogen or adsorped plasma. When normal pooled plasma is diluted 10 times with PSS to seek the above activating curve, the difference between the value of A taken prior to clotting and after sufficient clotting decreases to about 1/10th of that of the normal plasma. Clotting takes place partially and not uniformly through the sample, and the value A changes intermittently and not uniformly with time, then converging to a certain value. The abnormal plasma which has a longer clotting time also presents the same tendency.

Thus, the curve A for the above samples includes an additional wave component as if a higher frequency noise had been superimposed upon it. When clotting time in respect of such samples was measured by the first method mentioned above, the noise factor emphasized by differentiation caused the first differential curve dA/dt to exceed the threshold value several times so as to generate several signals representing false end points, thus making it difficult to judge the true end point.

As mentioned above, the advantage of the second method is that the clotting end point may be determined only by the optical properties of the sample. However, when the curve A includes a noise factor accompanying the coagulation process, the noise factor is differentiated twice and generates numerous zero crossings of the second differential from positive to negative, making it more difficult than in the first method to determine correctly the clotting end point. This is because its sensitivity toward the high frequency factor of noise is higher in the second differentiation than in the first differentiation.

In the prior art, a low pass filter has been used in an effort to eliminate noise, but the results have not been sufficiently satisfactory.

In one example normal plasma was diluted 10 times with PSS and APTT was checked. After the coagulant agent was added to the plasma, the value a measured in respect of optical properties of the sample gradually decreased with the time contrary to the case of normal plasma, slightly increased near the coagulation end point, and thereafter converged to a certain value.

In this test the second differential curve $d^2A/dt^2$ crossed the zero from positive to negative not just once at the true end point but many times.

Thus, when the second method mentioned above is used in testing such a sample, many of signals are generated representing false end points besides the one for the true end point and cause a great deal of errors.

SUMMARY OF THE INVENTION

The present invention was contrived in view of the defects of the conventional methods of measuring the blood clotting time as have been described above, and aims at offering an improved measurement of blood clotting time.

The present invention comprises in a blood clotting end point detector which includes means for monitoring an electrical signal representing the value of A of one or more optical properties of a blood plasma sample to which a coagulating agent has been added, means for deriving the first and the second differentials with respect to time of the value A, means for detecting the moment Ta when the second differential changes from negative to positive or becomes positive, means for detecting the moment Tb when the second differential next changes from positive to negative, means for deriving the difference (R) between the tangent to the curve A at the moment Ta and the curve A, means for determining whether the difference (R) or the integral, with respect to time from moment Ta to moment Tb, of the different (R) exceeds a predetermined threshold value, in which case moment Tb is taken as the true clotting end point.

The invention further comprises in a method of detecting the blood clotting end point of a blood plasma sample to which a coagulating agent has been added, which includes monitoring an electrical signal representing the value A of one or more optical properties of the sample, deriving the first and second differentials with respect to time of the value A, detecting the moment Ta when the second differential changes from negative to positive or becomes positive, detecting the moment Tb when the second differential next changes from positive to negative, and identifying the moment Tb as the true clotting end point only if at least one of the following two conditions are satisfied:

(i) the difference (R) between the tangent to the curve A at moment Ta and the curve A exceeds a first predetermined threshold value,
(ii) the integral, with respect to time from the moment Ta to the moment Tb, of the said difference (R) exceeds a second predetermined threshold value.

DETAILED DESCRIPTION

Figure 1:
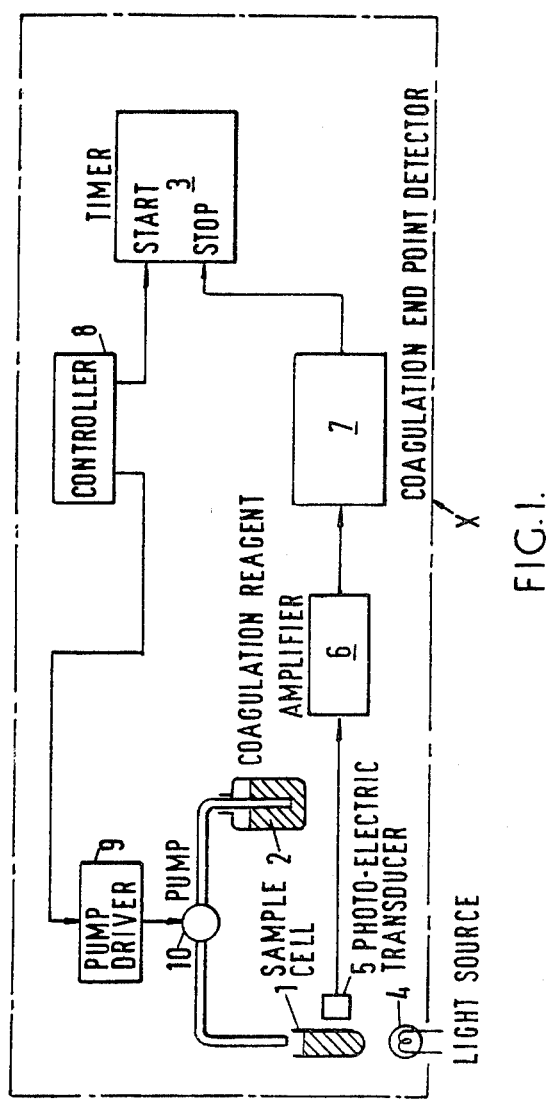
FIG. 1 shows one form of apparatus which may be used for carrying out the present invention.

In the accompanying drawings, FIG. 1 shows one form of apparatus which may be used for carrying out the present invention. A plasma sample (when using PT) or a plasma sample and Platelin-plus-activator (when using APTT) is placed in a sample cell 1. A controller 8 is then activated to start the test causing a pump driver 9 to operate a pump 10 to pump a predetermined quantity of coagulation reagent from a supply 2 into the cell 1. Simultaneously timer 3 is started. Light from source 4 is directed onto cell 1 and light scattered by the sample is received by a photo-electric transducer 5 whose output is amplified by amplifier 6 and fed to a coagulation end point detector 7 which in due course detects the end point and stops the timer 3. The timer thus records the clotting time.

Figure 2:
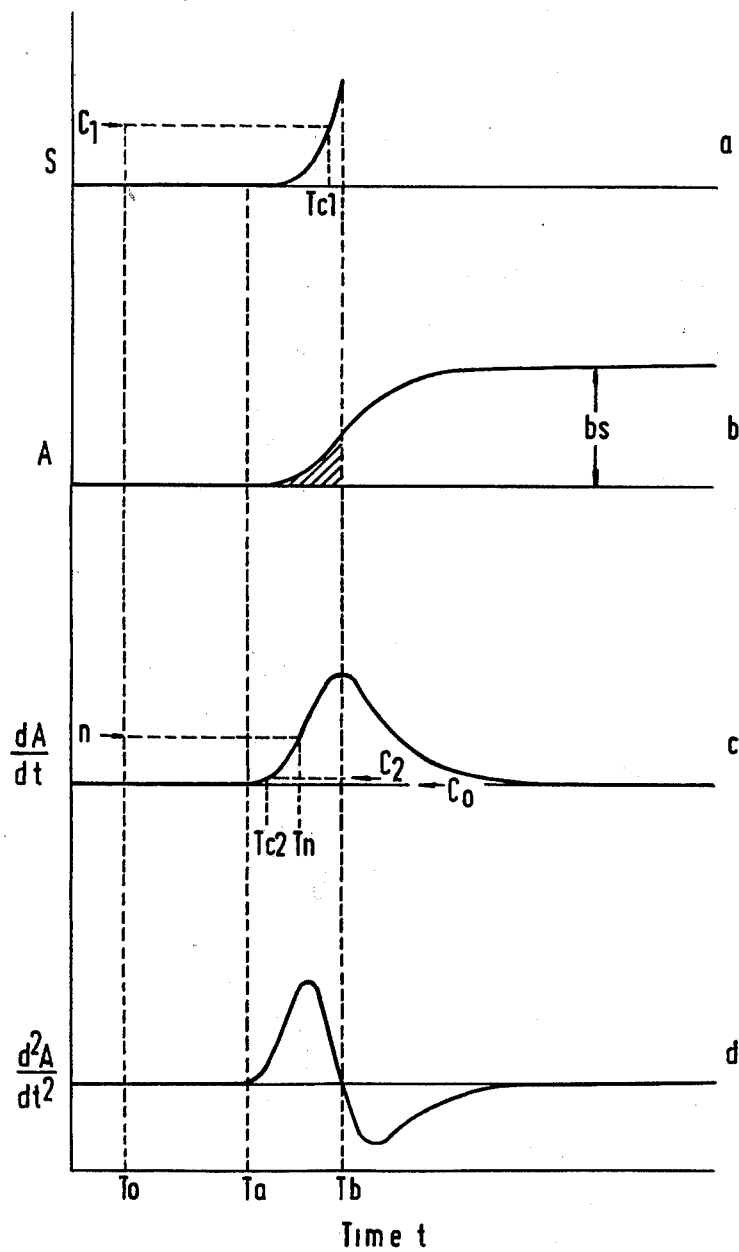
FIGS. 2 and 3 show typical examples of the curve A together with related curves, with and without noise respectively.
Figure 3:
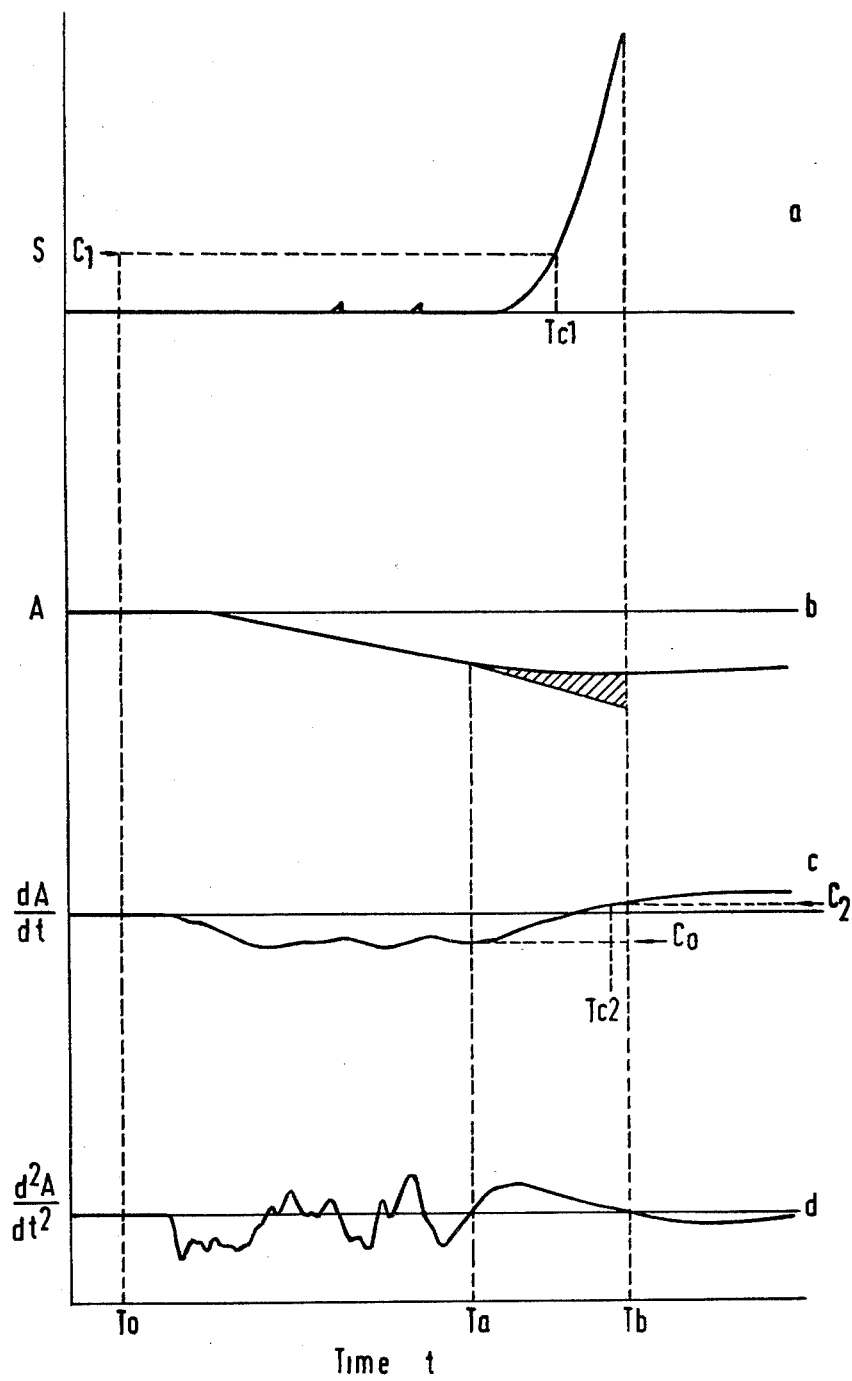

FIGS. 2 and 3 show curves relatedto the measurement of blood clotting time respectively in a case where a noise component is not included and where it is. FIG. 2 shows an example of PT measurement where coagulating agent has not been added to normal plasma and FIG. 3 shows an example where normal plasma has been diluted 10 times with PSS.

In FIGS. 2 and 3 time t is plotted on the abscissa and FIGS. 2b and 3b show the measured values A of one or more optical properties of the sample such as (1) absorbance, (2) transmittance or optical decay, (3) intensity of light scattered or its logarithmic value, (4) refractive index, (5) sum or difference of the above (1) to (4). FIGS. 2c and 3c show the first differentials with respect to time dA/dt of curves A, and FIGS. 2d and 3d their second differentials $d^2A/dt^2$. FIGS. 2a and 3a represent the areas indicated by the shading in FIGS. 2b and 3b, being the double integrals with respect to time of the first differentials shown in FIGS. 2c and 3c.

When coagulant agent is added to plasma when time t=T₀, the curve A takes the forms as shown in FIGS. 2b and 3b, the first differentials being shown in FIGS. 2c and 3c, and the second differentials in FIGS. 2d and 3d.

The movement when the second differential curve becomes positive or crosses zero from negative to positive is set as Ta, and the movement when it crosses zero from positive to negative is set as Tb. Thus, Tb represents the steepest point of the curve A. The second differential $d^2A/dt^2$ is positive between the time Ta and Tb, and this becomes one of the requirements for detecting the clotting end point in this example.

The value of the first differential dA/dt at time 5=Ta is recorded and the difference between this and the value Co of A at the same moment, i.e. (dA/dt−Co) is twice integrated with respect to time t from Ta to Tb to obtain the curves in FIGS. 2a and 3a whose ordinate S is given as $$S = \int_{Ta}^{Tb}\int_{Ta}^{Tb} (\frac{dA}{dt} - Co)dt\, dt$$

In other words, S is the twice integrated value of the difference (R) between the tangent to the curve A and A at time Ta, integrated with respect to time t from Ta to Tb, or the area between the respective times indicated by the oblique lines in FIGS. 2b and 3b. The moment when this double integral S exceeds a predetermined threshold value $C_1$ is noted as $Tc_1$, and one of the requirements for detecting the clotting end point is that double integral S be bigger than $C_1$.

In order to judge whether the slope at Tb in the curve A meets one of the requirements for detecting the clotting end point in the present embodiment, the time when the first differential curve dA/dt exceeds a predetermined threshold value $C_2$ is noted as $Tc_2$; the other of the requirements for detecting the clotting end point is that the first differential value be greater than $C_2$.

When at least one of the above two requirements for detecting the end point in the present example are satisfied, then ensuing Tb is taken as the end point. In the above method, (1) the time when the value of the second differential $d^2A/dt^2$ becomes positive from negative or from zero is set as Ta, and then the time it becomes negative from positive is set as Tb. In other words, the second differential $d^2A/dt^2$ becomes positive between Ta and Tb; (2) the area S covered by the shading in FIGS. 2b and 3b is bigger than $C_1$ at t=Tb; (3) the slope of curve A in FIGS. 2b and 3b or dA/dt in FIGS. 2c and 3c is bigger than $C_2$ at time Tb; (4) moment Tb at the steepest point of curve A is taken as the clotting end point.

Figure 4:
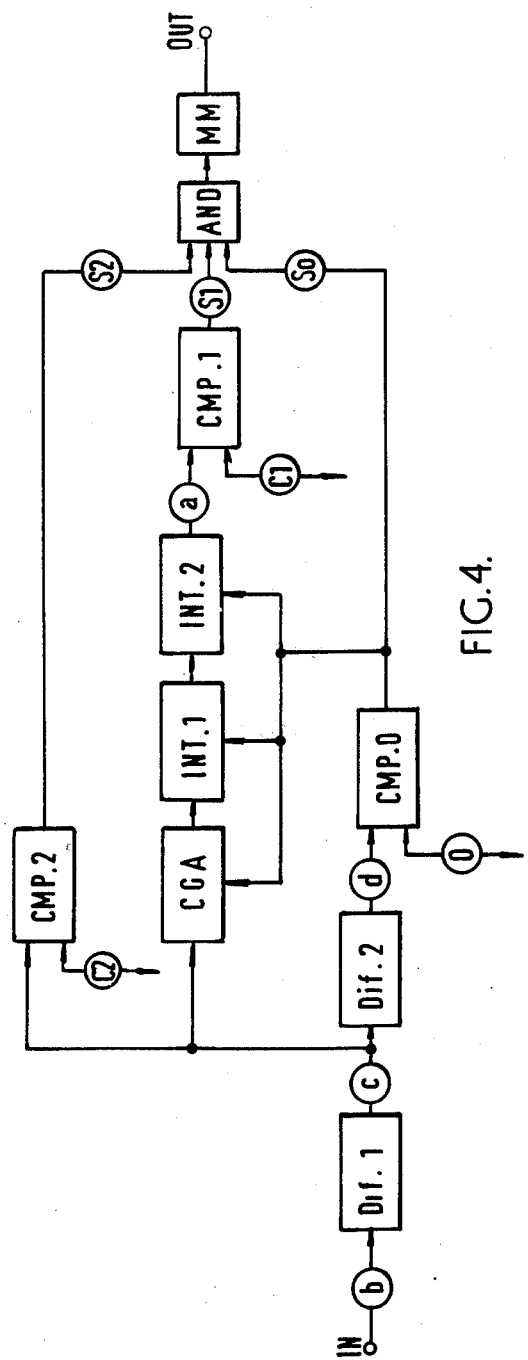
FIG. 4 shows diagrammatically one embodiment for carrying out the present invention.
Figure 5:
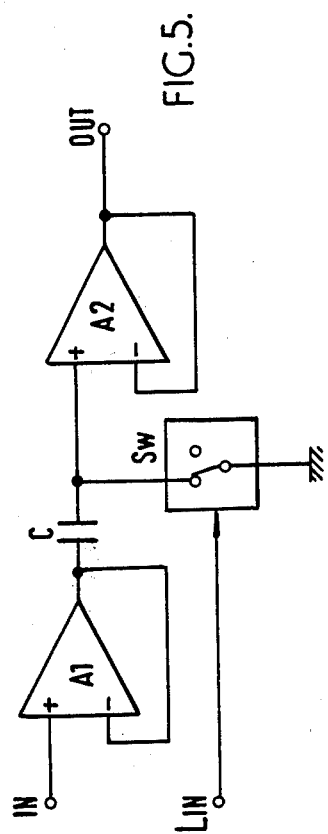
FIG. 5 shows a key-clamp type gate amplifier which may be used in the arrangement of FIG. 4.

This technique facilitates the reliable detection of the steepest portion of the curve A as the clotting end point without interference from noises generated during the coagulation process. A detailed description will now be given of a device for putting this method into practice, referring to FIGS. 4 and 5. In FIG. 4 IN indicates input a, b, c, d voltage curves corresponding to FIGS. 2a, 2b, 2c, 2d, or 3a, 3b, 3c and 3d respectively. Dif. 1 is the first differentiator, Dif. 2 the second differentiator, CMP. 0 the comparator unit to detect positive-negative voltage wave d of the second differentiation, its output $S_0$ becoming logical 1 when the comparator unit input becomes positive. CGA is an amplifier to clamp and gate the voltage wave c of the first differentiation, the details of which are shown in FIG. 5.

INT. 1 is the first integrator, INT. 2 the second integrator, CMP. 1 a comparator unit, CPM. 2 a comparator unit, AND an "and" circuit, MM the monostable multi-vibrator to generate detection pulses for the clotting end point when logical product of $S_0$, $S_1$, $S_2$ changes to 0 from 1, OUT the output terminals, 0 reference voltage and indicating zero voltage, $C_1$, $C_2$ reference voltages of predetermined values.

Signal A measured in respect of optical properties of the sample as shown in FIGS. 2b and 3b is applied as the signal b on the terminal IN to the left side of FIG. 4 and the once differentiated signal dA/dt of the input signal is obtained by the differentiator Dif. 1, its output curve being shown in FIGS. 2c and 3c. The signal c is again differentiated by the differentiator Dif. 2 to obtain second differential $d^2A/dt^2$ or the signal d, its waves being shown in FIGS. 2d and 3d. The signal d is compared with OV (zero volts) by the comparing unit CMP. 0 and the output signal $S_0$ from the comparator unit CMP. 0 becomes logical value 1 when the signal d (or the second differential $d^2A/dt^2$) is positive.

The first differential dA/dt from output of the differentiator Dif. 1, or signal c, is applied to key-clamp type gate amplifier CGA. One example of such an amplifier is shown in FIG. 5 wherein $A_1$ and $A_2$ denote buffer amplifiers, the output impedance of amplifier $A_1$ being extremely low and the input impedance of amplifier $A_2$ extremely high. Switch SW is for the clamp and the gate. When the logical value of the limit input LIN of Switch SW is zero, the input signal IN is not transmitted to output OUT, which is then 0. Output OUT in proportion to the changes in the input signal is obtained based on the input signal IN when the limit input LIN changes from the logical value 0 to 1. When the signal $S_0$ which changes in logical value to 1 when the second differential $d^2A/dt^2$ is positive is added to the limit input LIN of the switch SW to make logical value 1, output OUT in FIG. 5 is clamped to be OV against $C_0$, the first differential signal dA/dt applied to the input terminal.

Output OUT in FIG. 5 becomes proportional to the difference between the first differential signal dA/dt applied to the input terminal and $C_0$. When $S_0$ becomes the logical value 0, then the output OUT again becomes 0. In FIG. 4, the output from the key-clamp type gate amplifier is applied to the integrator INT. 1. The aforementioned signal $S_0$ is applied to the re-set input terminal of the integrator INT. 1. Accordingly, at the output of the integrator INT. 1 is obtained dA/dt $-C_0$ integrated with respect to time or the change of the first differentiation from Ta when logical value of $S_0$ becomes 1 from 0. Thus, this output equals the difference (R) between the tangent of the signal A curve at time Ta and A.

The output of the integrator INT. 1 is applied to the input of the integrator INT. 2, and integrated as for the integrator INT. 1 and the output from the integrator INT. 2 becomes proportional to the area covered by oblique lines in FIGS. 2b and 3b, or to the values of 2a and 3a. The output a from the integrator INT. 2 is applied to the input of the comparator unit CMP. 1 compared with the predetermined threshold value $C_1$. When the output from the integrator INT. 2 is bigger than $C_1$, then output $S_1$ of the comparator unit CMP. 1 becomes the logical value 1. Whether or not the area of FIG. 2a exceeds the predetermined threshold value $C_1$ is determined by the above. Then dA/dt is applied to the comparator unit CMP. 2 and compared with the predetermined value $C_2$. If dA/dt is bigger than $C_2$, then the output $S_2$ of the comparator unit CMP. 2 becomes the logical value 1. This will detect the slope in FIGS. 2b and 3b.

Outputs $S_0$, $S_1$ and $S_2$ from respective comparator unit CMP. 0, CMP. 1 and CMP. 2 are applied to the input of the AND circuit, the output of which will give their logical product. When the logical value for these output signals is 1, three requirements for detecting the clotting end point are met, and it suffices merely to seek the time when the output signal from the AND circuit becomes 0 from logical value 1, or when the logical product of $S_0$, $S_1$ and $S_2$ becomes 0 from 1 to seek the steepest portion of the curve A. Accordingly, the positive logical output from the AND circuit is fed to the input of monostable multivibrator MM which is triggered when the logical value changes from 1 to 0, the said multi-vibrator generating a signal indicating the clotting end point.

In the above example, two integrators INT. 1 and INT. 2 are used to perform integration of the first differential dA/dt twice to seek the area of the hatched portion under the curves in FIGS. 2b and 3b. This can be performed by one integration. That is, the difference (R) of the tangent of the curve A at time Ta and A may be compared directly with $C_1$. The requirement that the twice differentiated value $d^2A/dt^2$ should be positive between Ta and Tb is not necessarily needed if the time required for resetting the integrators INT. 1 and INT. 2 is not so long and the response from the comparator unit, CMP. 1, not so delayed. Accordingly, $S_0$ may be eliminated from the input of the AND circuit. Although $S_2$ is used to determine the slope at Tb of the curve A, it is possible to eliminate it from the AND circuit input depending on the sample. The above explanation made in respect of an analog circuit is also valid in respect of a digital circuit.

Figure 6:
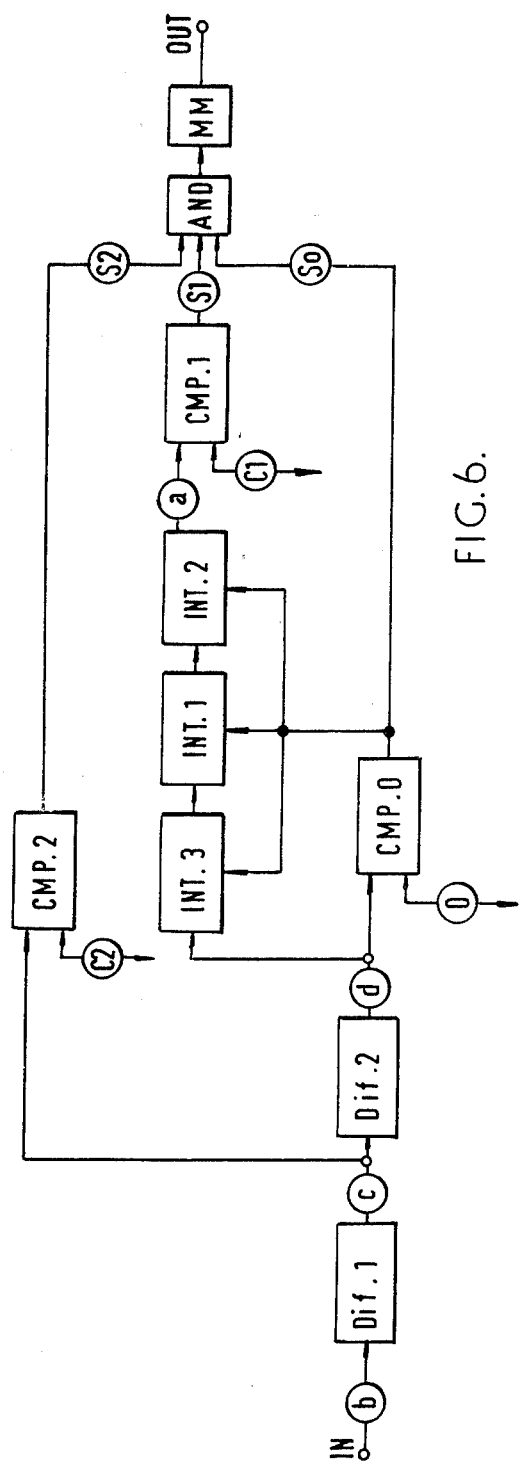
FIGS. 6 and 7 show diagrammatically two alternative embodiments for carrying out the present invention.

Difference (R) between the tangent to the curve A and A at Ta, or S obtained by integrating the difference (R) with respect to time t from Ta to Tb, can be determined by ways other than that mentioned above. One of such other ways is to seek the said difference (R) by double integrating the second differential curve $d^2A/dt^2$ from Ta to Tb or to seek S by triple integration. FIG. 6 shows an example embodying this method. Except for the circuit structure, the example of FIG. 6 functions identically as that of FIG. 4 when the portion between IN-OUT is regarded as a black box. In the method shown in FIG. 6, a third integrator, INT. 3, is provided in place of key-clamp type gate amplifier CGA of FIG. 4, the input of which is connected to the output d of the second differentiator, Dif. 2, while the reset input of the third integrator, INT. 3, is connected to the output S of the comparator unit, COMP. 0. The rest are the same as those in FIG. 4. That is, the second differential curve is used as the input for the third integrator INT. 3 in FIG. 6 instead of the first differential curve c used as the input for CGA whereas the output from the third integrator INT. 3 becomes the integrated value of the second differential curve integrated with respect to time from Ta to Tb, or (dA/dt−Co) in the method of FIG. 4, equal to CGA output in FIG. 4. The rest of the operations in FIG. 6 are identical to those in FIG. 4.

Figure 7:
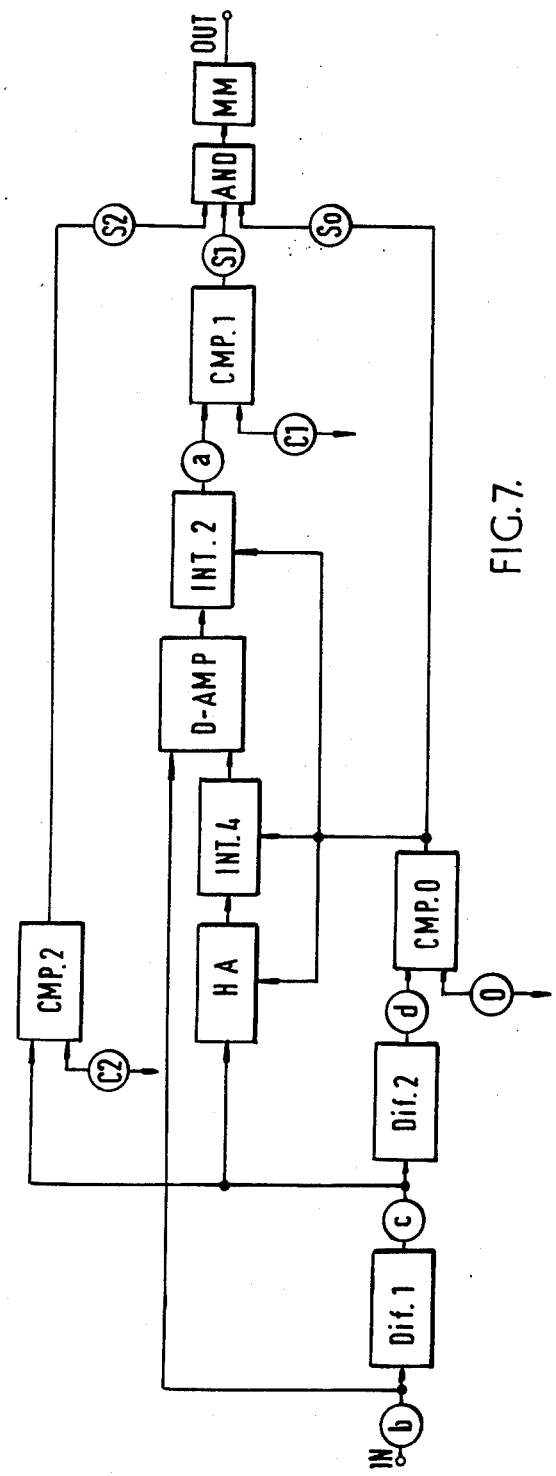

Another method is to integrate the once differential value [dA/dt]=Co at Ta with respect to time from Ta to Tb, its integrated value vs. time t curve becoming tangent to the curve A at Ta, and obtain the difference (R) by seeking the difference between A and the said integrated value, or obtain S by integrating (R) with respect to time from Ta to Tb. FIG. 7 shows an example of this method wherein functions are identical to those of FIG. 4 then the portion between IN and OUT is regarded a black box except for the circuit structure. The example in FIG. 7 uses hold amplifier HA, fourth integrator INT. 4 and differential amplifier D-AMP instead of key-clamp type gate amplifier, CGA, and the first integrator INT. 1. The input of hold amplifier HA is connected to the output c of the first differentiator Dif. 1, while limited input LIN of hold amplifier HA is connected similarly to output $S_0$ of the comparator unit CMP. 0.

Figure 8:
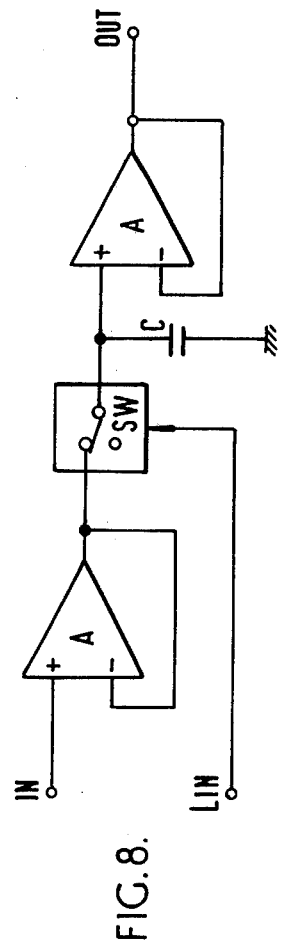
FIG. 8 shows a hold amplifier which may be used in the arrangement of FIG. 7.

One embodiment of the hold amplifier is shown in FIG. 8 wherein $A_1$ and $A_2$ are buffer amplifiers the output impedance of amplifier $A_1$ being extremely low while input impedance of amplifier $A_2$ extremely high.

When the logical value of limit input LIN of switch SW, which is for holding, is 0, input signal IN is transmitted to output OUT and the output is proportional to the input. When limit input LIN changes from logical value 0 to 1, the output OUT maintains the value which is proportional to the input signal at that moment unchanged by the capacitor C until the limit input LIN becomes 0 again. When the signal $S_0$ is applied to the limit input LIN of switch SW to change the logical value to 1 when the said twice differentiated value $d^2A/dt^2$ is positive, and $S_0$ becomes the logical value 1 from 0 at time Ta, then the output from the hold amplifier maintains the value proportional to the once differentiated value [dA/dt]=Co applied to the input terminal at Ta until the time Tb.

The input of the fourth integrator, INT.4, is connected to the output of the said hold amplifier HA while the reset input of the fourth integrator INT.4 is connected to the output $S_0$ of the comparator unit CMP.0. Accordingly, the output from the fourth integrator INT.4 becomes the integral value of the above $C_0$ integrated with respect to time from Ta to Tb. This integral value vs. time t curve is equivalent to the tangent of the curve A at time Ta.

The input on the sample side of differential amplifier D-AMP is connected to the IN terminal b on which the signal A is applied, whereas the input on the reference side is connected to the output of the above mentioned fourth integrator INT.4, and the difference between these two signals or the difference (R) between the tangent of the curve A and A at time Ta is obtained as the output. Accordingly, the output from the differential amplifier D-AMP is the same as the output of the first integrator INT.1. The rest of operations in the system of FIG. 7 are identical to those of FIG. 4.

Although the above description was made in with respect to analog circuits, the same effects are achieved by using a digital circuit when a digital signal A, converted by an analog-to-digital converter, is used.

As has been explained, the present invention offers excellent operational effects in accurately performing the blood clotting time measurement such as PT, APTT, and PTT by stably detecting as the clotting end point the steepest portion of the curve A, values measured of optical properties of the sample, - time t, free of noise effects. In FIG. 3a there can be seen two small pulses between moment To and moment Ta which represent integrated noise signals which have been rejected by the system, thereby avoiding indication of false end points.

The present method has similar effects in detecting the clotting end point when measuring the clotting time for platelet as for the blood clotting time.

We claim:

1. A method of detecting the blood clotting end point of a blood plasma sample to which a coagulating agent has been added, which includes:
   monitoring an electrical signal representing the value A of one or more optical properties of the sample,
   substantially continuously deriving the first and second differentials with respect to time of the electrical signals representing the value A,
   detecting the moment Ta when the second differential changes from negative to positive or becomes positive,
   detecting the moment Tb when the second differential next changes from positive to negative, and
   identifying the moment Tb as the true clotting end point only if at least one of the following two conditions are satisfied:
   (i) the difference (R) between the tangent to the electrical signals representing the value A at moment Ta and the value of said value A signals exceeds a first predetermined threshold value; and (ii) the integral, with respect to time from the moment Ta to the moment Tb, of said difference (R) exceeds a second predetermined threshold value.

2. A blood clotting end point detector which includes:
means for monitoring an electrical signal A representing the values of one or more optical properties of a blood plasma sample to which a coagulating agent has been added,
means coupled to said monitoring means for substantially continuously deriving the first and the second differentials with respect to time of the electrical signal A, and for generating respective signals representing the derived first and second differentials,
means responsive to the signal representing the second differential for detecting the moment Ta when the second differential of the electrical signal A changes from negative to positive or becomes positive,
means responsive to the signal representing the second differential for detecting the moment Tb when the second differential of the electrical signal A next changes from positive to negative,
means responsive to at least one of the respective signals representing the first and second differentials for deriving the difference (R) between the tangent to the electrical signal A at the time Ta and the electrical signal A,
means for determining whether the difference (R) or the integral, with respect to time from time Ta to time Tb, of the difference (R) exceeds a predetermined threshold value, in which case time Tb is taken as the true clotting end point.

3. A detector as claimed in claim 2, which includes means for twice integrating the second differential.

4. A detector as claimed in claim 2, which includes means for detecting whether the value of the second differential at moment Tb exceeds a predetermined threshold value, the time Tb being taken as the true end point only if said value is exceeded.

5. A detector as claimed in claim 2, wherein the means for deriving the difference (R) includes means for deriving the difference between the first differential and the value of the first differential at the time Ta.

6. A detector as claimed in claim 5, which includes means for twice integrating the difference (R) with respect to time from the time Ta to the moment Tb, the time Tb being taken as the true end point provided the twice integrated value exceeds a predetermined threshold value.

7. In a device where the blood clotting time is measured, displayed and recorded which includes an electronic timer which is started at the point when a coagulating agent is added to a plasma solution in a coagulation measuring sample cell, an amplifier for amplifying the electric signals generated as the light from a light source is applied to a photo-electric transducer via said sample cell, said amplified signals being designated as measured value A signals, and means for generating clotting and point detection signals for stopping said electronic timer, said clotting end point detection signals being obtained by applying a signal corresponding to said amplified signals to a clotting end point detector,
the improvement wherein said blood clotting end point detector comprises:
a first differentiator coupled to said amplifier for substantially continuously differentiating said measured value A signals with respect to time,
a second differentiator coupled to said first differentiator for substantially continuously differentiating the differentiated signals from said first differentiator,
means coupled to said second differentiator for detecting a first point where the second differential changes from negative to positive, said first point being set as the first standard point Ta, and for detecting a second point where the second differential changes from positive to negative, said second point being set as the second standard point Tb,
means for deriving the difference (R) between the tangent of the measured value A signals with time at the said first standard point Ta and the measured value A, and
means coupled to said deriving means for detecting when the said difference (R) exceeds a predetermined threshold value, or when the integrated value of the difference (R) with respect to time from the first standard point Ta to the second standard point Tb exceeds a predetermined threshold value, in which case the second standard point Tb is taken as the true clotting end point.

* * * * *

UNITED STATES PATENT AND TRADEMARK OFFICE
CERTIFICATE OF CORRECTION

PATENT NO. : 4,217,107
DATED : August 12, 1980
INVENTOR(S) : Yukio SAITO et al

It is certified that error appears in the above-identified patent and that said Letters Patent are hereby corrected as shown below:

COLUMN 3, line 12, "many of" should read --many--;

COLUMN 3, line 22, change "comprises in" to --comprises--;

COLUMN 3, line 41, change "comprises in" to --comprises--;

COLUMN 5, line 34, change "input" to -- and --;

COLUMN 5, line 35, before "a, b, c, d" insert --and--;

COLUMN 5, line 50, after "zero voltage" insert --and--;

COLUMN 5, line 54, change "on the terminal" to --to the terminal--;

COLUMN 5, line 54, after "IN" change "to" to --on--;

COLUMN 7, line 48, change "regarded a black box" to --regarded as a black box--;

COLUMN 8, line 29, "was made in with" should read --was made with respect--;

COLUMN 9, line 47 (claim 6), change "Ta to the moment Tb" to --Ta to the time Tb--.

Signed and Sealed this

Twenty-third Day of December 1980

[SEAL]

Attest:

SIDNEY A. DIAMOND

Attesting Officer

Commissioner of Patents and Trademarks